United States Patent [19]

Kamiyama et al.

[11] 4,237,329
[45] Dec. 2, 1980

[54] PROCESS FOR THE PRODUCTION OF ALKYLBENZENES

[75] Inventors: Setsuo Kamiyama, Kawagoe; Yukio Nagashima, Ooi; Hiroshi Furukawa, Ooi; Katsumi Kaneko, Ooi, all of Japan

[73] Assignee: Toa Nenryo Kogyo Kabushiki Kaisha, Tokyo, Japan

[21] Appl. No.: 29,629

[22] Filed: Apr. 13, 1979

Related U.S. Application Data

[63] Continuation-in-part of Ser. No. 867,165, Jan. 5, 1978.

[30] Foreign Application Priority Data

May 16, 1978 [JP] Japan ............................ 53/57152

[51] Int. Cl.$^3$ .................................................. C07C 5/22
[52] U.S. Cl. ...................................... 585/474; 585/475
[58] Field of Search ................................ 585/474, 475

[56] References Cited

U.S. PATENT DOCUMENTS

| | | | |
|---|---|---|---|
| 3,671,602 | 6/1972 | Inoue et al. | 585/474 |
| 3,763,260 | 10/1973 | Pollitzer | 585/475 |
| 3,769,360 | 10/1973 | Harper et al. | 585/474 |
| 3,780,122 | 12/1973 | Pollitzer | 585/474 |
| 3,849,340 | 11/1974 | Pollitzer | 252/455 Z |
| 3,873,632 | 3/1975 | Pollitzer | 585/481 |
| 3,926,782 | 12/1975 | Plank et al. | 585/467 |
| 4,120,908 | 10/1978 | Kamiyama et al. | 585/475 |
| 4,152,297 | 5/1979 | Kamiyama et al. | 252/455 Z |

FOREIGN PATENT DOCUMENTS

| | | |
|---|---|---|
| 4939652 | 12/1967 | Japan . |
| 509776 | 12/1968 | Japan . |
| 509777 | 12/1968 | Japan . |
| 509778 | 1/1969 | Japan . |
| 5021453 | 1/1969 | Japan . |
| 1634875 | 5/1969 | Japan . |
| 5016351 | 7/1969 | Japan . |
| 517654 | 7/1970 | Japan . |
| 1108177 | 4/1968 | United Kingdom . |

*Primary Examiner*—C. Davis
*Attorney, Agent, or Firm*—Rebecca Yablonsky

[57] ABSTRACT

This invention relates to a process for the production of alkylbenzenes, which comprises reacting benzene with at least one aromatic hydrocarbon substituted by alkyl groups and containing 9 or more carbon atoms, in the presence of an acid leached hydrogen form mordenite catalyst having a silica ($SiO_2$)/alumina ($Al_2O_3$) molar ratio of 15 to 21 and a sodium content of 0.05 weight % or less as $Na_2O$.

9 Claims, 2 Drawing Figures

PROCESS FOR THE PRODUCTION OF ALKYLBENZENES

CROSS-REFERENCE TO RELATED APPLICATIONS

This application is a continuation-in-part of Ser. No. 867,165 filed on Jan. 5, 1978.

This application is based on Japanese Patent Application 57152/78, filed May 16, 1978.

FIELD OF THE INVENTION

1. Background of the Invention

This invention relates to a process for producing alkylbenzenes from benzene and alkylaromatic hydrocarbons of 9 or more carbon atoms and is particularly concerned with a process for the production of ethylbenzene by the transalkylation of ethyl-containing aromatic hydrocarbons of 9 or more carbon atoms, with benzene.

2. Description of the Prior Art and Related Cases

Alkylbenzenes have been used widely as various industrial materials and, in particular, ethylbenzene is useful as a starting material for styrene monomer, which is produced mainly by ethylation of benzene. However, this method is uneconomical because of using expensive ethylene as a main starting material.

Many alternates have hitherto been proposed for producing ethylbenzene, by the transalkylation of an aromatic hydrocarbon containing the ethyl group such as ethyltoluene or diethylbenzene (instead of employing ethylene) with benzene. It is also known to use the zeolite type catalysts for the transalkylation reaction. For example, there have been proposed a method of producing ethylbenzene comprising transalkylation of an aromatic hydrocarbon containing the ethyl group and benzene using as a catalyst an acid leached hydrogen form mordenite obtained by removing alumina from mordenite to adjust the silica/alumina molar ratio to at least 21.5 (Japanese Patent Publication No. 3976/1974); a method of producing ethylbenzene from diethylbenzene and benzene by the use of $La^{+++}$ or $NH^+$ ion exchanged zeolite Y as a catalyst (U.S. Pat. No. 3,769,360); a method of producing ethylbenzene from a polyethylbenzene and benzene using a catalyst prepared by leaching with an acid solution a mordenite having a silica/alumina ratio of 12 to 30 to adjust the silica/alumina ratio to 40 or more and adding thereto copper, silver, gold and zirconium (Japanese Patent Public Disclosure No. 75490/1973); a method of producing ethylbenzene comprising transalkylation of diethylbenzene and benzene using a catalyst prepared by calcining mordenite dealkalized at least 80% in an oxygen atmosphere and subsequently partly decationizing so that the mordenite contains proton in a quantity of 0.2 to 0.5 equivalent per gram atom of aluminum (Japanese Patent Publication No. 16348/1975) and a method of producing ethylbenzene from diethylbenzene and benzene over a synthetic zeolite of crystalline aluminosilicate having a silica/alumina ratio of 5 to 100, which is called ZSM-5 (Japanese Patent Public Disclosure No. 5335/1975).

These methods, however, have the disadvantages that the reaction yield is low, complicated steps are required for the preparation of the catalyst and catalyst life is short.

It may further be noted that in U.S. Pat. No. 4,120,908 a method is disclosed for isomerizing xylenes in a $C_8$ aromatic hydrocarbon mixture by treatment with an acid leached hydrogen form mordenite catalyst having a silica to alumina molar ratio of 15 to 21. In the said process a portion of the ethylbenzene impurity present is disproportionated to benzene and diethylbenzene. In U.S. Ser. No. 867,165 filed on Jan. 5, 1978 by Setsuo Kamiyama et al a method is disclosed for stabilizing the said catalyst by pretreating it with liquid hydrocarbon, such as the feed to the isomerization process, in the absence of hydrogen at a temperature of about 20° to 270° C. at a pressure in the range of atmospheric to about 50 Kg/cm².

SUMMARY OF THE INVENTION

Applicants have made studies on catalysts capable of producing ethylbenzene through selective transalkylation of the ethyl group in the transalkylation of a mixture of ethyl aromatic hydrocarbons of 9 or more carbon atoms ($C_9$ or higher) and methyl aromatic hydrocarbons of $C_9$ or more with benzene and, consequently, have found that an acid leached hydrogen form mordenite having a controlled silica/alumina molar ratio has not only a very high activity as a catalyst for this reaction, but also a long catalyst life. The present invention is based on this finding.

That is to say, the gist of the present invention consists in a process for the production of alkylbenzenes, which comprises reacting an alkyl aromatic hydrocarbon of $C_9$ or more carbon atoms with benzene in the presence of an acid leached hydrogen form mordenite catalyst having a silica/alumina molar ratio of 15 to 21 and a sodium content of 0.05% by weight or less as $Na_2O$, that is, 0 to 0.05 wt. % as $Na_2O$.

DETAILED DESCRIPTION

Figure 1:
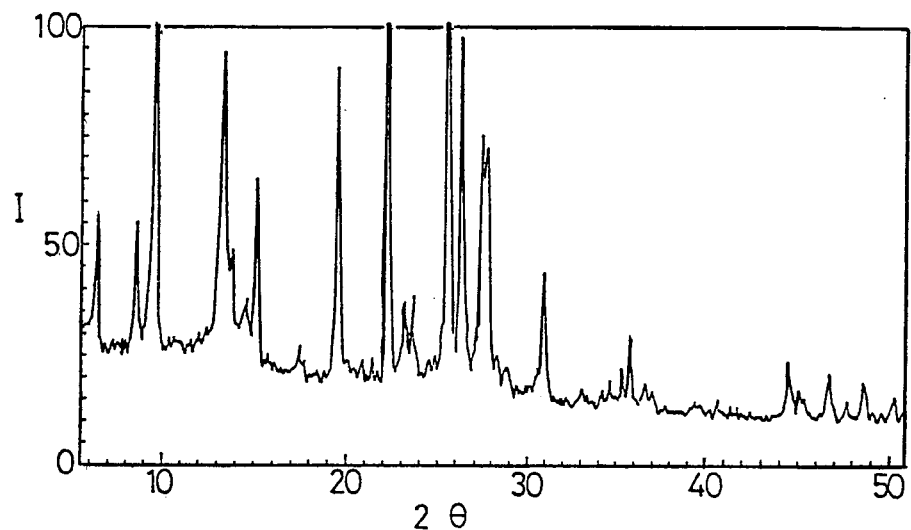
FIG. 1 and FIG. 2 show the X-ray diffraction patterns of the commercial mordenites used as starting material in Examples 1 and 4 respectively.

Mordenite is a crystalline aluminosilicate of zeolite type having the largest silica/alumina ratio, i.e. of 10, of the zeolites, and having unusual properties among the crystalline aluminosilicates of zeolite type, for example, excellent acid resistance and high heat resisting strength.

Among the mordenites, there are natural and synthetic ones, both of which may be used in the present invention. Synthetic mordenites are preferred. The commercially available synthetic mordenite is generally of sodium form, from which the catalyst of the present invention is prepared. That is, the acid leached hydrogen form mordenite is obtained by treating this synthetic mordenite with an acid to adjust the silica/alumina molar ratio to 15 to 21 and the sodium content to 0.05% by weight or less as $Na_2O$.

When a synthetic mordenite of sodium form is immediately acid treated, it is difficult to adjust the silica/alumina ratio and sodium content as described above in a well-balanced manner. Thus, it is desirable to treat a mordenite initially with an aqueous solution of $NH_4Cl$ or aqueous solution of mineral acid such as hydrochloric acid, nitric acid, sulfuric acid or phosphoric acid to remove most of the sodium and then treat (acid leach) with a mineral acid such as concentrated hydrochloric acid. The initial treatment is preferably carried out at a temperature of from room temperature to 90° C. for 24 to 120 hours and the acid leaching is preferably carried out at a temperature of from 60° to 90° C. for 24 to 48 hours.

By the initial treatment of a sodium form mordenite, the sodium ion is exchanged by $NH_4$ ion or hydrogen ion and, thus, this is sometimes called "$NH_4$ form mordenite" or "hydrogen form mordenite." The $NH_4$ form mordenite is converted into hydrogen form mordenite by calcining at a temperature of about 400° to 600° C. The acid leached hydrogen form mordenite having a controlled silica/alumina ratio and sodium content is then washed with water until the anion of the acid used is not detected, dried at a temperature of 100° C. or higher and calcined at 450° to 550° C. in air, thus producing the catalyst used in the present invention. The catalyst prepared in this way has substantially the same crystalline structure as the original mordenite, which can be confirmed by measurement of the X-ray diffraction pattern thereof. The catalyst of the present invention is particularly effective when it has a surface area of 400 to 500 $m^2/g$ and a pore volume of 0.20 to 0.45 cc/g. In addition, the acid leached hydrogen form mordenite of the present invention can be blended with alumina or silica-alumina gel followed by molding, if desired.

The alkyl aromatic hydrocarbon to be reacted with benzene according to the present invention includes various aromatic hydrocarbons. In particular, as a starting material in the case of producing ethylbenzene in the process of the invention, there are used ethyl aromatic hydrocarbons of $C_9$ or more carbon atoms, preferably ethyltoluene, diethylbenzene, etc. Mixtures of aromatic hydrocarbons of $C_9$ or higher including these hydrocarbons may be used. Ethyltoluene or diethylbenzene is difficult to obtain commercially, as a pure chemical, but is contained in a considerable quantity in hydrocarbon fractions obtained by thermal cracking, catalytic cracking or reforming of petroleum. These hydrocarbon fractions contain large amounts of benzene, toluene and xylene (BTX) which are separated and recovered, often by solvent extraction. With BTX, aromatic hydrocarbons of $C_9$-$C_{10}$ such as ethyltoluene, diethylbenzene, etc. are simultaneously extracted. Therefore, the use of the aromatic hydrocarbons of $C_9$-$C_{10}$ remaining after the separation and recovery of BTX from the above described extract, as a starting material, is very important from an economic point of view since credits are obtained for byproduct utilization.

That is to say, an advantage of the present invention consists in using not only ethyl aromatic hydrocarbons of 9 or more carbon atoms such as ethyltoluene and diethylbenzene, but also mixtures of aromatic hydrocarbons of $C_9$ or higher including these aromatic hydrocarbons. In particular, the present invention is more effective when using as a starting material mixtures of aromatic hydrocarbons consisting mainly of $C_9$-$C_{10}$ obtained by solvent extraction of hydrocarbon fractions produced by thermal cracking, catalytic cracking or reforming of petroleum to give an extract with BTX and then separating BTX from the extract.

The composition of the above described mixture of aromatic hydrocarbons consisting mainly of $C_9$-$C_{10}$ comprises; in general, 20 to 35% by weight of ethyltoluene, 20 to 35% by weight of trimethylbenzene, 10 to 35% by weight of diethylbenzene, 10 to 25% by weight of ethylxylene and a trace of 10% by weight of other hydrocarbons.

The present invention is characterized in that when using the mixture of aromatic hydrocarbons having the above described composition as a starting material, benzene is selectively transalkylated with ethyltoluene and diethylbenzene. That is, alkylbenzenes having two or more methyl groups, for example, trimethylbenzene and ethylxylene are less reactive in the transalkylation with benzene, as compared with ethyltoluene and diethylbenzene, so there is formed a very small quantity of xylene having a boiling point similar to that of ethylbenzene and thus separation and recovery of ethylbenzene from the reaction products can readily be carried out. This feature is advantageous and unexpected.

The present invention is illustrated by way of example in the case of using, as a starting material, aromatic hydrocarbons of $C_9$ or higher having ethyl groups mainly, but is not intended to be limited thereby. It is possible to use as a starting material aromatic hydrocarbons having alkyl groups of more carbon atoms than the ethyl group, such as propyl group, butyl group and dodecyl group and in this case, propylbenzene, butylbenzene, etc. can effectively be produced in a manner analogous to the production of ethylbenzene.

When a mixture of ethyltoluene, diethylbenzene, etc. with an aromatic hydrocarbon of $C_9^+$ having a propyl group or butyl group is used as a starting material and reacted with benzene, ethylbenzene, propylbenzene and butylbenzene can respectively be produced in high yield without the reactions suppressing each other. These alkylbenzenes have such different boiling points that they can readily be separated and recovered by distillation.

In the present invention, the benzene/aromatic hydrocarbon molar ratio is defined by mols benzene/mols alkyl groups to be transferred = 1 to 10, preferably 2 5. Depending on whether one uses polyalkylbenzenes such as diethylbenzene and the like, or mixtures of aromatic hydrocarbons, one will adjust the amounts of reagents accordingly, i.e., to satisfy the above described range.

The reactor used may be of any type, for example, a fixed bed or a moving bed and the reaction may be carried out in gaseous phase or liquid phase. The reaction temperature is generally 120° to 300° C., preferably 180° to 250° C. and the reaction pressure is generally normal pressure to 200 $Kg/cm^2$, preferably 5 to 100 $Kg/cm^2$. The liquid hour space velocity (LHSV) is generally 0.1 to 20 $hour^{-1}$, preferably 0.5 to 10 $hour^{-1}$.

For the purpose of preventing deposits of carbon, etc. from forming on the surface of the catalyst which would cause lowering of the activity thereof, it is desirable to carry out the reaction in the presence of hydrogen in a proportion of 10 mols or less, e.g., 1 to 10 mols, preferably 2 to 5 mols per 1 mol of a mixed starting material comprising benzene and the aromatic hydrocarbon.

The catalyst used in the present invention is preferably first subjected to a treatment comprising contacting it with the aromatic hydrocarbon or mixed starting material of the same with benzene in the absence of hydrogen in the reaction system. By this treatment, the life of the catalyst can be prolonged considerably. The conditions are: a temperature of room temperature to 270° C., preferably 50° to 250° C., a pressure of normal pressure to 50 $Kg/cm^2$, preferably 5 to 20 $Kg/cm^2$, an LHSV of 1 to 5 $hour^{-1}$, preferably 2 to 3 $hour^{-1}$ and a reaction time of 1 to 50 hours, preferably 3 to 20 hours.

According to the present invention, therefore, ethylbenzene in particular can effectively be produced from ethyl aromatic hydrocarbons of 9 or more carbon atoms such as ethyltoluene, diethylbenzene, etc. Furthermore, ethylbenzene can also be produced in high yield from cheap and available mixtures of heavy aromatic hydrocarbons of $C_9$ or higher which remain after the recovery of BTX and which do not have a utility at the present time and this is worthwhile commercially and economically.

When using as a raw material mixtures of methyl aromatic hydrocarbons such as for example trimethylbenzene, durene and the like and aromatic hydrocarbons having an ethyl group, propyl group, butyl group and the like, trimethylbenzene, durene and the like can readily be separated and recovered from the reaction products in the present invention because the intermolecular transfer of the methyl group is much less than for the ethyl group, propyl group, butyl group and the like.

The following examples are given in order to illustrate the present invention in detail without limiting the same, in which % means weight percent unless otherwise indicated.

EXAMPLE 1

A commercially available hydrogen form synthetic mordenite (made by Norton Co., commercial name: Zeolon 200 H) having the X-ray diffraction pattern shown in FIG. 1, a silica/alumina molar ratio of 12.6 and an $Na_2O$ content of 0.32% was treated with concentrated hydrochloric acid at 90° C. for 24 hours, washed with water until the chloride ion was not detected, dried at 110° C. for 3 hours and calcined at 500° C. in air for 6 hours, thus to prepare an acid leached hydrogen form mordenite catalyst having an X-ray diffraction pattern similar to that of FIG. 1, a silica/alumina molar ratio of 20.7, a surface area of 498 $m^2/g$, a pore volume of 0.43 cc/g and an $Na_2O$ content of 0.04%.

The so obtained catalyst was charged to a cylindrical reactor and then subjected to transalkylation reactions (Run Nos. 1 to 5) with benzene using diethylbenzene as a starting material under the conditions shown in Table 1. Additionally, pressure was atmospheric, LHSV was 1.0 hour$^{-1}$ and a molar ratio of hydrogen/mixed starting materials of 3.0 was used. After two hours from the start of the reaction, the reaction product was taken and subjected to analysis with the results shown in Table 1.

TABLE 1

| Starting Materials | Run No. 1 | 2 | 3 | 4 | 5 |
|---|---|---|---|---|---|
| Benzene (%) | 53.8 | 53.8 | 53.8 | 74.8 | 36.2 |
| Diethylbenzene (%) | 43.0 | 43.0 | 43.0 | 23.5 | 59.5 |
| Others (%) | 3.2 | 3.2 | 3.2 | 1.7 | 4.3 |
| Benzene/Ethyl Group to be transformed (molar ratio) | 2.1 | 2.1 | 2.1 | 5.5 | 1.0 |

TABLE 1-continued

| Starting Materials | Run No. 1 | 2 | 3 | 4 | 5 |
|---|---|---|---|---|---|
| Reaction Temperature (°C.) | 225 | 210 | 200 | 200 | 200 |
| Conversion of Diethylbenzene (%) | 58.9 | 43.9 | 29.4 | 75.5 | 17.1 |
| Content of Ethylbenzene in Product (%)* | 35.7 | 30.1 | 20.7 | 29.9 | 13.7 |
| Ethylbenzene Purity in $C_8$ Aromatic Hydrocarbons | 95.7 | 98.6 | 98.9 | 99.4 | 98.3 |

*Unreacted starting materials are contained in reaction product.

EXAMPLE 2

With the same catalyst as that of Example 1 and mixed starting materials comprising 53.6% of benzene, 43.8% of ethyltoluene and 2.6% of other $C_9$-$C_{10}$ aromatic hydrocarbons (benzene/ethyl group to be transformed molar ratio=1.9), an experiment (Run No. 6) was carried out at a reaction temperature of 200° C., a reaction pressure of normal pressure, an LHSV of 1.0 hour$^{-1}$ and a hydrogen/mixed starting materials molar ratio of 3.0 similarly to Example 1, thus obtaining the following results:

| | |
|---|---|
| Conversion of Ethyltoluene | 64.9% |
| Content of Ethylbenzene* in Product | 17.2% |
| Ethylbenzene Purity in $C_8$ Aromatic Hydrocarbons | 97.1% |

*Unreacted mixed starting materials were contained in the reaction product.

EXAMPLE 3

The commercially available hydrogen form synthetic mordenite used in Example 1 was treated with concentrated hydrochloric acid in the same manner as in Example 1 to prepare various acid leached hydrogen form mordenite catalysts having the properties shown in Table 2.

The resulting catalysts were charged to a cylindrical reactor and the reactions were carried out therein at a reaction temperature of 200° C., an LHSV of 1.0 hour$^{-1}$ and a pressure of normal pressure by continuously feeding mixed starting materials of an aromatic hydrocarbon fraction retained after extracting and recovering BTX from a reformed oil and comprising a trace amount of o-xylene, 24.5% of ethyltoluene, 23.0% of trimethylbenzene, 31.0% of diethylbenzene and 21.5% of ethylxylene with benzene in a proportion of 3.0 mols per mol of the ethyl groups to be transformed in the aromatic hydrocarbon fraction in the presence of hydrogen in a proportion of 3.0 mols to 1 mol of the mixed starting materials (Run Nos. 7 to 13). After 2 hours from the start of the reaction, the reaction product was taken and subjected to analysis to obtain the results shown in Table 2:

TABLE 2

| Run No. | Silica/Alumina (molar ratio) | Catalyst Surface Area $m^2/g$ | Catalyst Pore Volume (cc/g) | $Na_2O$ Content (%) | Conversion (%) Ethyltoluene | Tri-methyl-benzene | Diethyl-Benzene | Ethyl-xylene | Content of Ethylbenzene in Product (%)** | Ethylbenzene Purity in $C_8$ Aromatic Hydrocarbons(%) |
|---|---|---|---|---|---|---|---|---|---|---|
| 7* | 12.6 | 346 | 0.13 | 0.32 | 12.2 | 4.8 | 18.1 | 9.7 | 5.9 | 79.1 |
| 8* | 14.2 | 368 | 0.19 | 0.09 | 41.8 | 7.1 | 50.5 | 19.3 | 12.7 | 83.7 |
| 9 | 15.0 | 405 | 0.22 | 0.05 | 62.1 | 8.8 | 72.7 | 23.2 | 17.7 | 89.2 |
| 10 | 17.2 | 438 | 0.29 | 0.04 | 66.6 | 9.1 | 74.8 | 24.1 | 17.7 | 90.0 |
| 11 | 20.7 | 498 | 0.43 | 0.04 | 68.9 | 9.5 | 76.9 | 24.6 | 17.9 | 90.1 |
| 12* | 22.7 | 535 | 0.47 | 0.03 | 55.3 | 9.0 | 59.1 | 24.7 | 14.1 | 86.2 |

TABLE 2-continued

| Run No. | Silica/ Alumina (molar ratio) | Catalyst Surface Area m²/g | Catalyst Pore Volume (cc/g) | Na₂O Content (%) | Ethyl-toluene | Conversion (%) Tri-methyl-benzene | Diethyl-Benzene | Ethyl-xylene | Content of Ethylbenzene in Product (%)** | Ethylbenzene Purity in C₈ Aromatic Hydrocarbons(%) |
|---|---|---|---|---|---|---|---|---|---|---|
| 13* | 29.3 | 542 | 0.47 | 0.03 | 32.2 | 8.6 | 38.2 | 22.6 | 10.0 | 82.1 |

Note:
*Comparative Example
**Containing unreacted starting materials

As is apparent from the results of Table 2, ethyltoluene and diethylbenzene are selectively transalkylated with benzene to give a high ethylbenzene content, i.e. about 90%, in the C₈ aromatic hydrocarbon fraction of the reaction product by the use of the acid leached hydrogen type mordenite catalyst having a silica/alumina molar ratio of 15 to 21. Depending upon the intended use of the ethylbenzene, this C₈ aromatic hydrocarbon fraction can be used directly or high purity ethylbenzene can readily be purified and recovered from this fraction.

EXAMPLE 4

Figure 2:
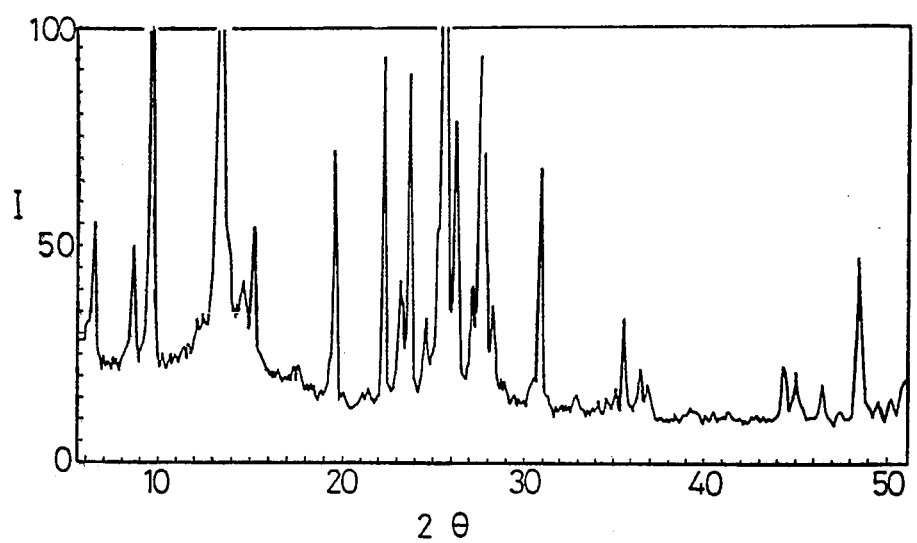

A commercially available NH₄ form synthetic mordenite (made by Shokubai Kasei K. K., 2352-084) having the X-ray diffraction pattern shown in FIG. 2 and a silica/alumina molar ration of 10.0 in powdered form was calcined at 500° C. to convert it to the hydrogen form, treated with concentrated hydrochloric acid at 90° C. for one day and night, washed with water until the chloride ion was not detected and dried at 110° C. for 3 hours, thus obtaining an acid leached hydrogen form mordenite having a silica/alumina molar ratio of 19.5 and an Na₂O content of 0.04%. The resulting acid leached hydrogen form mordenite was mixed with 5% of silica-alumina gel as a binder, formed, dried and calcined at 500° C. in air for 6 hours to prepare a catalyst.

Then the procedure of Example 3 was repeated except that this catalyst was used (Run No. 14), thus obtaining the following results:

| | |
|---|---|
| Conversion of Ethyltoluene | 66.5% |
| Conversion of Trimethylbenzene | 9.3% |
| Conversion of Diethylbenzene | 74.5% |
| Conversion of Ethylxylene | 24.5% |
| Content of Ethylbenzene in Product* | 17.6% |
| Ethylbenzene Purity in C₈ Aromatic Hydrocarbons | 89.3% |

*Unreacted mixed starting materials were contained in the reaction product.

EXAMPLE 5

The same acid leached hydrogen form mordenite catalyst as that of Run No. 11 of Example 3 was charged to a cylindrical reactor in which the same mixed starting materials as those of Example 3 were first contacted with the catalyst at a temperature of 225° C., an LHSV of 2 hour⁻¹ and a pressure of 20 Kg/cm² for 20 hours. Then a reaction test was carried out for a long time by feeding the mixed starting materials continuously to the reactor at a temperature of 210° C., an LHSV of 1.0 hour⁻¹ and a pressure of 20 Kg/cm² in the presence of hydrogen in a proportion of 3.0 mols to 1 mol of the mixed starting materials (Run No. 15). In addition, the procedure of Run No. 15 was repeated except omitting the pretreatment of the catalyst with the mixed starting materials according to Run No. 15 (Run No. 16).

For comparison, on the other hand, the procedures of Run Nos. 15 and 16 were repeated except using the same catalyst (with a low silica/alumina ratio) as that of Run No. 7 of Example 3 (Run Nos. 17 and 18).

TABLE 3

| Run No. | Silica/ Alumina (molar ratio) | Pretreatment | Reaction Time (Hr) | Ethyl-toluene | Conversion (%) Tri-methyl-benzene | Diethyl-Benzene | Ethyl-xylene | Content of Ethylbenzene in Product (%)* | Ethylbenzene Purity in C₈ Aromatic Hydrocarbon(%) |
|---|---|---|---|---|---|---|---|---|---|
| 15 | 20.7 | Effected | 10 | 65.1 | 9.0 | 71.9 | 23.5 | 17.6 | 89.9 |
| | | | 30 | 63.8 | 8.9 | 73.7 | 23.8 | 17.9 | 89.8 |
| | | | 60 | 64.6 | 9.1 | 72.7 | 23.8 | 17.5 | 90.3 |
| | | | 100 | 64.1 | 9.1 | 73.1 | 23.4 | 17.6 | 89.9 |
| 16 | 20.7 | None | 10 | 63.8 | 8.8 | 70.1 | 23.0 | 17.3 | 89.3 |
| | | | 30 | 60.1 | 8.3 | 69.1 | 22.1 | 17.0 | 89.2 |
| | | | 100 | 55.1 | 7.9 | 63.9 | 20.6 | 16.7 | 87.8 |
| 17 | 12.7 | Effected | 10 | 10.9 | 4.6 | 17.1 | 8.8 | 5.6 | 79.0 |
| | | | 30 | 8.2 | 4.0 | 15.3 | 6.9 | 5.0 | 78.7 |
| 18 | 12.7 | None | 10 | 11.0 | 4.7 | 17.0 | 8.6 | 5.5 | 78.1 |
| | | | 30 | 5.2 | 3.1 | 10.0 | 4.3 | 2.2 | 77.0 |

Note:
*Unreacted starting materials are contained in the reaction product.

It will clearly be understood from the results of Table 3 that the activity of the catalyst can be maintained for a long time by the pretreatment of the catalyst according to the present invention.

What is claimed is:

1. A process for the production of ethylbenzene, which comprises reacting benzene with a mixture of substantially C₉-C₁₀ aromatic hydrocarbons comprising polymethylbenzene, and ethyltoluene and/or diethylbenzene, in the presence of an acid leached hydrogen form mordenite catalyst having a silica (SiO₂)/alumina (Al₂O₃) molar ratio of 15 to 21 and a sodium content of 0.05 weight % or less as Na₂O and in the presence of hydrogen.

2. The process of claim 1 in which the reaction conditions are a temperature of 120° to 300° C., a pressure of atmospheric to 200 Kg/cm² and a LHSV of 0.1 to 20 hour⁻¹.

3. The process of claim 1 in which hydrogen is employed in a ratio of 2 to 5 mols per mol of the mixed starting material comprising benzene and the aromatic hydrocarbons.

4. The process of claim 1 in which a mixture of substantially $C_9$-$C_{10}$ aromatic hydrocarbons is used which is recovered in separating benzene, toluene and xylene (BTX) from the extracted fraction obtained by solvent extraction of the hydrocarbons produced by thermal cracking, catalytic cracking or reforming of petroleum.

5. The process of claim 1 in which the benzene/aromatic hydrocarbon molar ratio is defined by mols benzene/mols alkyl groups to be transferred = 1 to 10.

6. The process of claim 5 in which the ratio is 2 to 5.

7. A process for the production of ethylbenzene which comprise first treating an acid leached hydrogen form mordenite catalyst having a silica ($SiO_2$)/alumina ($Al_2O_3$) molar ratio of 15 to 21 and a sodium content of 0.05 weight % or less as $Na_2O$, with aromatic hydrocarbons at a temperature of ambient to 270° C., a pressure of atmospheric to 50 Kg/cm$^2$ and an LHSV of 1 to 5 hour$^{-1}$ for 1 to 50 hours in the absence of hydrogen; and then reacting in the presence of said catalyst benzene with a mixture of substantially $C_9$-$C_{10}$ aromatic hydrocarbons comprising polymethylbenzene, and ethyltoluene and/or diethylbenzene, in the presence of hydrogen, the molar ratio of benzene/aromatic hydrocarbon being mols benzene/mols alkyl groups to be transferred = 2 to 5.

8. The process of claim 7 in which the aromatic hydrocarbons used in the absence of hydrogen have the same composition as the feed mixture used in the presence of hydrogen.

9. The process of claim 1, 4 or 7 in which the substantially $C_9$-$C_{10}$ aromatic hydrocarbon mixture contains approximately:
   20-35 weight % ethyltoluene
   20-35 weight % trimethylbenzene
   10-35 weight % diethylbenzene
   10-25 weight % ethylxylene and
   a trace to 10% other hydrocarbons.

* * * * *